US007335634B2

(12) United States Patent
Walter et al.

(10) Patent No.: US 7,335,634 B2
(45) Date of Patent: Feb. 26, 2008

(54) USE OF PLASMA PROTEINS CONCENTRATES CONTAINING VWF WITH A HIGH PROPORTION OF HIGH MOLECULAR WEIGHT MULTIMERS

(75) Inventors: Olaf Walter, Goldingen (CH); Hans-Peter Hauser, Marburg (DE)

(73) Assignee: CSL Behring GmbH, Marburg (DE)

( * ) Notice: Subject to any disclaimer, the term of this patent is extended or adjusted under 35 U.S.C. 154(b) by 244 days.

(21) Appl. No.: 11/121,046

(22) Filed: May 4, 2005

(65) Prior Publication Data

US 2005/0282735 A1 Dec. 22, 2005

(30) Foreign Application Priority Data

May 5, 2004 (EP) ................... 04010721

(51) Int. Cl.
*A01N 37/18* (2006.01)
(52) U.S. Cl. ................. 514/2; 514/12; 514/2; 435/69.6
(58) Field of Classification Search ...................... None
See application file for complete search history.

(56) References Cited

U.S. PATENT DOCUMENTS

| 5,408,039 | A | 4/1995 | Burnouf-Radosevich et al. |
| 5,869,617 | A | 2/1999 | Fisher et al. |
| 6,288,613 | B1 | 5/2001 | Fisher et al. |
| 6,531,577 | B1 | 3/2003 | Kaersgaard et al. |
| 2002/0058625 | A1 | 5/2002 | Mitterer et al. |
| 2004/0132654 | A1 | 7/2004 | Kumpe et al. |

FOREIGN PATENT DOCUMENTS

| EP | 1 405 863 A1 | 9/2003 |
| WO | WO 98/38220 | 9/1998 |
| WO | WO-98/38220 | 9/1998 |

OTHER PUBLICATIONS

Smith et al.; "Continuous Infusion Therapy With Very High Purity Von Willebrand Factor Concentrate in Patients With Severe Von Willebrand Disease"; Blood Coagulation and Fibrinolysis, vol. 8, No. 1, pp. 6-12, (1997).
Hampton et al.; The Use of Two Plasma Derived Factor VIII Concentrates in Type 2 A Von Willebrand's Disease (VWD); Blood, vol. 102, No. 11, p. 99b, (2003).
Lethagen et al.; "Pharmacokinetics and Hemostatic Effect of Different Factor VIII/Von Willebrand Factor Concentrates in Von Willebrand's Diease Type III"; Annals of Hematology, vol. 65, No. 6, pp. 253-259, (1992).
Facon; "Acquired Type II Von Willebrand's Disease Associated With Adrenal Cortical Carcinoma"; British Journal of Haematology, vol. 80, No. 4, pp. 488-494, (1992).
Gill et al.; "Successful Treatment of Urgent Life-or Limb-Threatening Hemorrhages in Patients With Von Willebrand Disease (VWD) Treated With Factor VIII/VWF Concentrate (Humate-P(R))"; Blood, vol. 96, No. 11, pp. 567a, (2000).
Lethagen et al.; "A Comparative In Vitro Evaluation of Six Von Willebrand Factor Concentrates"; Haemophilla, vol. 10, No. 3, pp. 243-249, (2004).
Takahashi et al.; "Heat-Treated Factor VIII/Von Willebrand Factor Concentrate in Platelet-Type Von Willebrand's Disease"; Haemostasis, vol. 17, No. 6, pp. 353-360, (1987).
Walter et al.; "Dependence of Von Willebrand Factor Activity in Relation to the High-Molecular-Weight Von Willebrand Factor Multimers in Various VWF/FVIII-Concentrates"; Blood, vol. 100, No. 11, (2002).
Mohri et al.; "Acquired Von Willebrand Syndrome: Its Pathophysiology, Laboratory Features and Management"; Journal of Thrombosis and Trombolysis, vol. 15, No. 3, pp. 141-149, (2003).
Rinder et al.; "Acquired Von Willebrand's Disease: A Concise Review"; American Journal of Hematology, vol. 54, No. 2, pp. 139-145, (1997).
Barstad, R. Marius et al.; "Protamine Sulphate Inhibits Platelet Membrane Glycoprotein Ib-von Willebrand Factor Activity", 2000 Schattauer Verlag, Stuttgart, Thromb Haemost 2000; 83:334-7.
Budde, U., et al., "Luminographic Detection of von Willebrand Factor Multimers in Agarose Gels and on Nitrocellulose Membranes", Thrombosis and Haemostatis, F.K. Schattauer Verlagsegsellschaft mbH (Stuttgart) 63(2) 312-315 (1990).
Fressinaud, Edith, et al., "Screening for von Willebrand Disease with a New Analyzer Using High Shear Stress: A Study of 60 Cases", The American Society of Hematology, Blood, vol. 91, No. 4 Feb. 15, 1998: pp. 1325-1331.
Heyde, E.C., "Correspondence: Gastrointenstinal Bleeding in Aortic Stenosis", The New England Journal of Medicine, Jul. 24, 1958, pp. 196-197.
Metzner, H. J., et al., "Characterization of factor VII/von Willebrand factor concentrates using a modified method of von Willebrand factor multimer analysis", Haemophilia (1998), 4 (Suppl. 3), 25-32.
Neugebauer, B. M., et al., "A Collagen Binding Assay: An Additional Method for von Willebrand Factor Activity in Therapeutic Concentrates", Letters to the Editor, Thromb Haemost 2002; 88:871-2.
Ozkisacik, E., et al., "Demopressin usage in elective cardiac surgery", J. Cardiovasc Surg 2001; 42:741-7.
Pareti, F. I., et al., "Proteolysis of von Willebrand Factor and Shear Stress-Induced Platelet Aggregation in Patients with Aortic Valve Stenosis", American Heart Association, Inc., Apr. 17, 2000; pp. 1290-1295.
Veyradier, Agnès, et al., "Abnormal von Willebrand Factor in Bleeding Angiodysplasias of the Digestive Tract", Alimentary Tract, Gastroenterology 2001; 120:346-353.
Veyradier, Agnès, et al., "Acquired von Willebrand Syndrome: from Pathophysiology to Management", Review Article, 2000 Schattauer Verlag, Stuttgart, Thromb Haemost 2000; 834:175-82.

(Continued)

*Primary Examiner*—Hope Robinson
(74) *Attorney, Agent, or Firm*—Finnegan, Henderson, Farabow, Garrett & Dunner, L.L.P.

(57) ABSTRACT

Use of plasma proteins concentrates containing VWF with a high proportion of high molecular weight multimers prevents a bleeding diathesis and reduces pre-, peri- and post-operative blood loss in acquired Von Willebrand syndromes such as in cardiovascular diseases requiring surgical procedures, especially those requiring extracorporeal circulation.

22 Claims, No Drawings

OTHER PUBLICATIONS

Vincentelli, André et al., "Acquired von Willebrand Syndrome in Aortic Stenosis", The New England Journal of Medicine 349:4, Jul. 24, 2003.

Suiter, T., et al., "Comparison of von Willebrand factor activities measured by ristocetin cofactor assay and two different VWF-collagen-binding-assays in VWF/FVIII-concentrates", NIA—Exhibition Area, Supplement to the Journal of Thrombosis and Haemostasis Jul. 2003 (ISSN 1740 3340).

Walter, O., et al., "Determination of High-Molecular-Weight von Willebrand factor multimers and their impact on specific VWF-activities in VWF/FVIII-concentrates", NIA—Exhibition Area, Supplement to the Journal o f Thrombosis and Haemostasis Jul. 2003 (ISSN 1740 3340).

Warkentin, Theodore E., et al., "Gastrointestinal Bleeding, Angiodysplasia, Cardiovascular Disease, and Acquired von Willebrand Syndrome", Transfusion Medicine Reviews, vol. 17, No. 4 Oct. 2003: pp. 272-286.

Warkentin, Theordore E., et al., "Aortic stenosis and bleeding gastrointestinal angiodysplasia: is acquired von Willebrand's disease the link?", Hypotesis, The Lancet, vol. 340: Jul. 4, 1992, pp. 35-37.

USE OF PLASMA PROTEINS CONCENTRATES CONTAINING VWF WITH A HIGH PROPORTION OF HIGH MOLECULAR WEIGHT MULTIMERS

This application claims priority to European Application No. 04010121.1, filed May 5, 2004.

Use of plasma proteins concentrates containing VWF with a high proportion of high molecular weight multimers prevents a bleeding diathesis and reduces pre-, peri- and postoperative blood loss in acquired Von Willebrand syndromes, for example, in cardiovascular diseases requiring surgical procedures, especially those requiring extracorporeal circulation.

1. Field of the Invention

The present invention relates to the prophylactic and therapeutic use of plasma protein concentrates which contain Von Willebrand Factor (VWF) with a high proportion of VWF high molecular weight multimers to prevent a bleeding diathesis in acquired Von Willebrand syndrome (VWS), preferentially that of VWS type 2A, as in cardiovascular diseases, especially aortic stenosis, or during extracorporeal circulation (ECC). By the prophylactic use of suitable VWF concentrates, the number of bleeding episodes and blood loss during surgical procedures such as cardiac surgery with extracorporeal circulation (ECC) can be minimized.

2. Background of the Invention

Humans have evolved an intricate hemostatic system designed to maintain blood in a fluid state under physiologic conditions but primed to react to vascular injury by sealing the defect in the vessel wall. The first steps of this sealing process, called primary hemostasis, involves VWF mediated binding of platelets to the site of vessel injury. The reactions include adhesion of platelets to the cut end of a blood vessel, spreading of adherent platelets on the exposed subendothelial surface, secretion of stored platelet constituents, and formation of large platelet aggregates. In a process called secondary hemostasis, the platelet membrane becomes available for adsorption and concentration of blood clotting factors resulting in the formation of a fibrin network that reinforces the otherwise fragile platelet plug.

VWF plays an essential role in the first steps of primary hemostasis. VWF does not bind to intact endothel but attaches via its collagen receptor to exposed subendothelium. This attachment leads to an unfolding of VWF bringing its A1 domain in a conformation capable of binding to platelet GP1b. Whereas VWF can also interact with other platelet receptors like GPIIb/IIIa, and whereas platelets can also adhere to the subendothelium via other receptors like specific collagen receptors in conditions of high shear rate which occur for example in stenosed vessels, the VWF-A1 platelet GPIb interaction is essential for tethering platelets to the injured endothelium. After the binding of platelets via GPIb to VWF-A1, the GPIIb/IIIa receptor is exposed on the platelet surface, which binds to fibrinogen and leads to the subsequent aggregation of platelets.

VWF is produced in endothelial cells and in megakaryocytes as a prepropeptide of 2813 amino acids in length, consisting of a signal peptide of 22 amino acids, a propeptide of 741 amino acids, and a mature VWF of 2050 amino acids.

After cleavage of the signal peptide in the endoplasmatic reticulum a C-terminal disulfide bridge is formed between two monomers of VWF. During further transport through the secretory pathway, 12 N-linked and 10 O-linked carbohydrate side chains are added. More importantly, a propeptide of 741 amino acids length is cleaved off by the enzyme furin in the late Golgi apparatus and VWF dimers multimerize via N-terminal disulfide bridges. The propeptide as well as the high-molecular-weight multimers of VWF (VWF-HMWM) are stored in the Weibel-Pallade bodies of endothelial cells or in the α-Granules of platelets.

Once secreted into plasma the protease ADAMTS13 cleaves VWF within the A1 domain of VWF. Plasma VWF therefore consists of a whole range of multimers ranging from single dimers of 500 kDa to multimers consisting of up to more than 20 dimers of a molecular weight of over 10,000 kDa. The VWF-HMWM hereby having the strongest hemostatic activity can be measured in ristocetin cofactor activity (VWF:RCo). The higher the ratio of VWF:RCo/VWF antigen, the higher the relative amount of high molecular weight multimers. Alternatives for the determination of the VWF-HMWM content are the determination of the ratio of VWF collagen binding assay (VWF:CB) to VWF antigen, which is also decreased when VWF-HMWM are missing, or the elevation of closure time in the platelet function analyzer PFA-100, or a gel based multimer analysis.

Defects in VWF are causal to Von Willebrand disease (VWD), which is characterized by a more or less pronounced bleeding phenotype. VWD type 3 is the most severe form in which VWF is completely missing, VWD type 1 relates to a quantitative loss of VWF and its phenotype can be very mild. VWD type 2 relates to qualitative defects of VWF and can be as severe as VWD type 3. VWD type 2 has many sub forms, some of them being associated with the loss or the decrease of high molecular weight multimers. Von Willebrand syndrome type 2a (VWS-2a) is characterized by a loss of both intermediate and large multimers. VWS-2B is characterized by a loss of highest-molecular-weight multimers.

The invention relates to the surprising discovery that in acquired VWS leading to a bleeding diathesis especially in cardiovascular disease (e.g. aortic stenosis), blood loss can be reduced or prevented by administration of plasma protein concentrates containing VWF with a high proportion of high-molecular-weight multimers.

The association of bleeding events with cardiac diseases has been discussed in several publications in the past.

Heyde (N Engl J Med. 1958; 259:196) described an unexplained association of aortic stenosis with GI bleeding events (Heyde's syndrome).

Several authors have published on the use of desmopressin to treat bleeding associated with cardiac surgery with conflicting results. Ozkisacik et al. 2001, J Cardiovasc Surg 42:741-7) found that a patient group undergoing cardiopulmonary bypass treated with desmopressin did not differ with regard to blood loss as well as to the number of blood transfusions from the control group, though the desmopressin group had elevated VWF levels. As desmopressin causes either a slight elevation or a transient fall in blood pressure and a compensatory increase in heart rate, it is not recommended for therapy in cardiac surgery and patients with coronary artery insufficiency.

Warkentin et al. (Lancet, 1992 340:35-7) proposed that a stenotic artery valve could lead to a reversible deficiency of the largest multimers of VWF, a defect equivalent to VWS-2a.

Pareti et al. (Circulation 2000, 102:1290-1295) found that the correction of aortic valve stenosis leads to increased shear-induced platelet aggregation with a concomitant rise in VWF HMWM. Pareti found that in cardiac patients with a bleeding tendency the VWF HMWM pattern was as abnormal as in those patients without a bleeding tendency but despite these data concludes that treating hemorrhagic complications in cardiac patients with suitable VWF concentrates to normalize the plasma levels of large VWF multimers might be beneficial without showing data to prove the efficacy of such a treatment.

Veyradier et al. (Thromb. Haemost. 2000, 84:175-82) lists as one of the causes for acquired VWS, high shear stress due to aortic stenosis. As the therapeutic option, valve replacement is suggested. Infusion of desmopressin and VWF concentrate may be only in part effective and are regarded as insufficient alone due to the short half life of VWF.

Veyradier et al. (Gastroenterology 2001, 120: 346-353) add further proof of the link between digestive bleeding and the loss of VWF-HMWM as 8 of 9 patients with bleeding GI angiodysplasia had reduced levels of VWF HMW multimers.

Vincentelli et al., (NEJM 2003, 349: 343-349) show that as early as 3 hours after valve replacement VWF-HMWM reappear. The authors also relate elevated bleeding diathesis to the loss of VWF-HMWM due to high shear rates caused by aortic stenosis and go on to point out that therapeutic possibilities for the control of bleeding are limited and recommend valve replacement as the best therapeutic option.

Warkentin (Transfusion Medicine Reviews 2003, 17:272-286) discusses therapeutic options for acute bleeding secondary to angiodysplasia in cardiovascular disease; the use of somatostatin, octreotide and rFVIIa is discussed. The author states that in the indication of cardiovascular disease there is little experience with traditional therapies for VWD like desmopressin and FVIII/VWF concentrates and goes on to point out that factor concentrates are relatively deficient in the VWF-HMWM and may therefore provide minimal if any benefit.

In conclusion, the prior art suggests that high shear rates due to vascular stenosis lead to a preferential loss of VWF-HMWM resulting in a bleeding phenotype similar to that of VWS-2A. No successful prevention of this bleeding diathesis with VWF concentrates has been shown to date. Therefore, also no teaching on patient selection, dosing, treatment modality (bolus, repeated doses, continuous infusion and the timing and duration) for prevention of such bleeding diathesis with VWF concentrates is found in the prior art.

Due to mechanical turbulences, extra corporeal circulation (ECC) also used in cardiac surgery can per se also add to the loss of VWF-HMWM. Further, it has been demonstrated that the interaction of blood with the synthetic surfaces of the heart-lung machine during ECC increases platelet activation and therefore alpha granule release. Therefore, in the immediate postoperative phase, these storage organelles are depleted for VWF and can no longer contribute to primary hemostasis. Further, the infusion of protamine to neutralize heparin after cardiac surgery negatively affects the binding of VWF to platelets (Barstad et al. 2000, Thromb Haemost 83:334-7). All these mechanisms negatively influence primary hemostasis and add to the beneficial effect of prophylactic pre-, peri- and postoperative VWF concentrate infusion in cardiac surgery.

It is the essence of this invention that it is surprisingly found that by following certain patient selection criteria, prophylaxis and treatment guidelines, VWF concentrates can be successfully used to prevent a bleeding diathesis and to reduce pre-, peri- and postoperative blood loss in acquired Von Willebrand syndromes preferentially in cardiovascular diseases requiring surgical procedures, especially those requiring extracorporeal circulation.

As it is necessary to reconstitute the normal HMWM-VWF content, not all VWF concentrates are equally well suited for the prevention of bleeding in the described indications. For example Humate®/Haemate® (Aventis Behring GmbH, Emil-von-Behring-Straβe 76, 35041 Marburg, Germany) has been shown to have a content of VWF-HMWM of 83%-94% as compared to 100% of VWF-HMWM in normal human blood plasma, whereas most other currently commercially available VWF concentrates contain only 3.9% to 35.9% of HMWM-VWF as compared to 100% of HMWM-VWF in normal human blood plasma (Metzner et al., Haemophilia 1998, Walter et al. J. Thromb. Haemost., 2003). With regard to the present invention therefore, VWF concentrates in some embodiments contain more than 75%, in other embodiments more than 50%, or in yet other embodiments less than 50% of VWF-HMWM as compared to 100% HMWM-VWF in normal human blood plasma.

DETAILED DESCRIPTION OF THE INVENTION

The invention is about preventing and treating a bleeding diathesis due to acquired VWS associated with concomitant loss of VWF-HMWM and or impaired platelet GPIb-VWF interaction in clinical conditions such as cardiovascular or renal diseases, for instance, those requiring ECC and or protamine sulfate administration, by applying certain guidelines in selecting patients amenable to such therapy.

In clinical conditions leading to a specific loss of the VWF-HMWM e.g. by unphysiologically high shear rates as in acquired (e.g. in valve stenosis) or inherited (e.g. ventricular septal defect (VSD), patent ductus arteriosus (PDA)) cardiovascular disease patients can be selected by way of unlimiting example in mild aortic stenosis to have a mean gradient of 0-25 mm Hg, in moderate aortic stenosis 25-50 mm Hg, and in severe aortic stenosis >50 mm Hg.

Alternatively, patients may be selected by selecting patients with a loss of VWF-HMWM being diagnosed by
- a ratio of VWF:RCo/VWF:Ag of <0.8, or in some embodiments <0.7, or in still other embodiments <0.6; OR
- a ratio of VWF:CB/VWF-Ag of <0.8 or in some embodiments <0.7, or in still other embodiments <0.6; OR
- or an elevated closure time in the PFA-100® (Dade Behring Diagnostics) using the collagen/ADP cartridge of >than 100 s (3.2% citrated blood) or >than 120 s (3.8% citrated blood); OR
- a gel based multimer analysis showing a proportion of VWF-HMWM of less than 80%, or of less than 70%, or of even less than 60%.

Such selected patients can be treated by intravenous infusion of a VWF concentrate with a proportion of VWF-HMWM of less than 50%, or more than 50%, or even more than 75%.

Dosing VWF in those patients should lead in some embodiments to a VWF:RCo of more than 70%, or in other embodiments of a VWF:RCo of more than 100%, or in still other embodiments of a VWF:RCo of more than 150%, with continous infusion (CI), or by way of bolus infusion with subsequent repeated dosing with a VWF:RCo to trough levels of more than 70%, or to trough levels of more than 100%, or to trough levels of even more than 150%, or if an initial bolus is combined with subsequent CI to trough levels of more than 70%, or trough levels of more than 100%, or trough levels of even more than 150%.

Administering such dose of such VWF concentrates pre-, peri- and postoperatively in surgery by bolus injection, repeated dosing, or even by way of continuous infusion removes the cause for the specific loss of VWF-HMWM in this application and in other ECC applications.

As used herein, the terms "treat" and "treatment" refer to any administration according to the present invention to reduce symptoms already present in a patient, and to preventative or prophylactic administration, for example, to reduce or prevent the onset or recurrence of symptoms that a patient is at risk for developing the symptoms.

As used herein, administration of the instant plasma protein concentrates "in conjunction with" another procedure, intervention, treatment, or administration merely means that the two administrations are both given as part of a patient's overall course of treatment for a medical condition. For example, plasma protein concentrates given "in conjunction with" another treatment may be given before or after that other treatment, or during a different medical procedure or by a different means of administration than that other treatment.

It is understood that, as used herein, all numbers and percentages are approximate, being subject to both measurement error and rounding according to procedures known to those of ordinary skill in the art.

EXAMPLE 1

Patients with an aortic stenosis about to undergo surgery for valve replacement are subjected to the following analysis:

1. A patient having a pressure gradient of >50 mm Hg is considered for treatment. To determine the mean gradient of transvalvular pressure gradient, echocardiographic systems or other suitable methods are used.

2. Optionally patients with pressure gradients of >25 mm Hg are further selected according to VWF multimer analysis
   a. VWF:RCo/VWF-Ag (according to the method described in Metzner at al., Haemophilia 1998 4:25-32); OR
   b. VWF:CB/VWG-Ag Ag (according to the method described in Neugebauer et al., Thromb Haemost 2002 88:871-2); OR
   c. PFA-100 elevated closure time in collagen/ADP cartridge of or (Fressinaud et al., Blood. 1998 91:1325-31); OR
   d. SDS-PAGE Ag (according to the method described in Budde et al., Thromb Haemost 1990 63(2):312-5).

In another embodiment of the invention, patients having
   a) a ratio of VWF:RCo/VWF:Ag <0.6; OR
   b) a ratio of VWF:CB/VWF:Ag <0.6; OR
   c) an elevated closure time of the collagen/ADP cartridge in the PFA-100 of more than 100s (3.2% citrated blood) or more than 120 s (3.8% citrated blood); OR
   d) a proportion of VWF-HMWM of less than 60% in a gel based multimer analysis are then subjected to continuous infusion (CI) of a suitable VWF-concentrate dosed to at least a VWF:RCo of more than 70%, or a VWF:RCo of more than 100%, or a VWF:RCo of even more than 150% with CI, or by way of bolus infusion with subsequent repeated dosing with a VWF:RCo trough level of more than 70%, or a VWF:RCo trough level of more than 100%, or a VWF:RCo trough level of even more than 150%, 30 minutes prior to the start of surgery. Repeated dosing after the initial bolus injection can also be replaced by CI dosed to maintain a trough level of more than 70%, or a trough level of more than 100%, or a trough level of even more than 150%. CI of the suitable VWF-concentrate is stopped about 4 hours after the end of surgery.

The invention claimed is:

1. A method of treating bleeding diathesis and/or reducing at least one of pre-, peri-, or post-operative blood loss, comprising administering von Willebrand Factor to a patient in need thereof in an amount sufficient to treat bleeding diathesis and/or sufficient to reduce at least one of pre-, peri-, or post-operative blood loss in said patient, wherein the von Willebrand Factor comprises more than 35.9% high molecular weight multimers.

2. The method according to claim 1, wherein the patient has a cardiovascular disease requiring surgery.

3. The method according to claim 1, wherein the patient suffers from at least one clinical condition generating unphysiologically high shear rates.

4. The method according to claim 3, wherein the condition is one or more of aortic stenosis, ventricular septal defects, patent ductus arteriosus, or an inherited cardiovascular disorder characterized by gradients of pressure.

5. The method according to claim 1, wherein the patient suffers from von Willebrand Syndrome type 2A.

6. The method according to claim 1, wherein the patient is selected for treatment based upon:
   a) a ratio of von Willebrand Factor ristocetin co-factor activity to von Willebrand Factor antigen activity (VWF:RCo to VWF:Ag) of less than 0.8;
   b) a ratio of von Willebrand Factor collagen binding activity to von Willebrand Factor antigen activity (VWF:CB to VWF:Ag) of less than 0.8;
   c) an elevated closure time in a platelet function analyzer assay comprising a collagen/ADP cartridge, wherein the time is greater than 100 seconds with 3.2% citrated blood or greater than 120 seconds with 3.8% citrated blood; or
   d) a proportion of less than 80% von Willebrand Factor multimers based upon an electrophoresis analysis.

7. The method according to claim 6, wherein the patient is selected for treatment based upon:
   a) a VWF:RCo to VWF:Ag ratio of less than 0.7;
   b) a VWF:CB to VWF:Ag ratio of less than 0.7; or
   c) a proportion of less than 70% von Willebrand Factor multimers based upon an electrophoresis analysis.

8. The method according to claim 7, wherein the patient is selected for treatment based upon:
   a) a VWF:RCo to VWF:Ag ratio of less than 0.6;
   b) a VWF:CB to VWF:Ag ratio of less than 0.6; or
   c) a proportion of less than 60% von Willebrand Factor multimers based upon an electrophoresis analysis.

9. The method according to claim 1, wherein the von Willebrand Factor is administered in conjunction with a procedure or intervention using extra corporal circulation.

10. The method according to claim 1, wherein the von Willebrand Factor is administered in conjunction with protamine to neutralize heparin.

11. The method according to claim 1, wherein the von Willebrand Factor comprises more than 50% high molecular weight multimers.

12. The method according to claim 11, wherein the von Willebrand Factor comprises more than 75% high molecular weight multimers.

13. The method according to claim 12, wherein the von Willebrand Factor comprises from 83% to 94% high molecular weight multimers.

14. The method according to claim 1, wherein the von Willebrand Factor is administered by continuous infusion, leading to VWF:RCo of more than 70%.

15. The method according to claim 14, wherein the continuous infusion leads to a VWF:RCo of more than 100%.

16. The method according to claim 15, wherein the continuous infusion leads to a VWF:RCo of more than 150%.

17. The method according to claim 1, wherein the von Willebrand Factor is administered by bolus infusion and subsequent repeated dosing leads to a trough level of VWF:RCo of more than 70%.

18. The method according to claim 17, wherein the bolus infusion and subsequent repeated dosing leads to a trough level of VWF:RCo of more than 100%.

19. The method according to claim 18, wherein the bolus infusion and subsequent repeated dosing leads to a trough level of VWF:RCo of more than 150%.

20. The method according to claim 1, wherein the von Willebrand Factor is administered by bolus infusion and subsequent continuous infusion leads to a trough level of VWF:RCo of more than 70%.

21. The method according to claim 20, wherein the bolus infusion and subsequent continuous infusion leads to a trough level of VWF:RCo of more than 100%.

22. The method according to claim 21, wherein the bolus infusion and subsequent continuous infusion leads to a trough level of VWF:RCo of more than 150%.

* * * * *